(12) United States Patent
Jackman et al.

(10) Patent No.: US 6,352,998 B2
(45) Date of Patent: Mar. 5, 2002

(54) PHARMACEUTICAL COMPOSITIONS

(75) Inventors: Martin Jackman, Allschwil; Xue-Ping Popp, Basel, both of (CH); Friedrich Richter, Grenzach-Wyhlen (DE); Fritz Schmook, Vienna (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/767,656

(22) Filed: Jan. 23, 2001

Related U.S. Application Data

(63) Continuation of application No. 09/488,283, filed on Jan. 20, 2000, which is a continuation of application No. 09/302,763, filed on Apr. 30, 1999, now abandoned, which is a continuation of application No. 08/836,091, filed on Apr. 25, 1997, now abandoned.

(51) Int. Cl.$^7$ ............................................. A61K 31/445
(52) U.S. Cl. ....................................................... 514/291
(58) Field of Search ................................. 514/291, 947, 514/949

(56) References Cited

U.S. PATENT DOCUMENTS

| | | | |
|---|---|---|---|
| 5,061,700 A | 10/1991 | Dow et al. ................. | 514/169 |
| 5,143,918 A | * 9/1992 | Bochis et al. | |
| 5,385,907 A | 1/1995 | Asakura et al. ............. | 514/291 |

FOREIGN PATENT DOCUMENTS

| | | |
|---|---|---|
| DE | 44 18 115 | 12/1994 |
| EP | 0027286 | 4/1981 |
| EP | 0184162 | 6/1986 |
| EP | 0 315 978 | 5/1989 |
| EP | 0323042 | 7/1989 |
| EP | 0 423 714 | 4/1991 |
| EP | 0427680 | 5/1991 |
| EP | 0465426 | 1/1992 |
| EP | 0474126 A1 | 3/1992 |
| EP | 0 483 842 | 5/1992 |
| EP | 0 484 936 | 5/1992 |
| EP | 0532088 | 3/1993 |
| EP | 0532089 | 3/1993 |
| EP | 0569337 | 11/1993 |
| EP | 0626385 | 11/1994 |
| WO | 9113899 | 9/1991 |
| WO | 9119495 | 12/1991 |
| WO | 9305059 | 3/1993 |
| WO | 9511039 | 4/1995 |

OTHER PUBLICATIONS

Chemical Abstracts, vol. 122, No. 12; Mar. 20, 1995, Columbus, Ohio, US; Abstract No. 142531, (abstracting JP,A,06 183 970 (Fujisawa Pharmaceutical Co., JP) Jul. 5, 1994).

* cited by examiner

Primary Examiner—William R. A. Jarvis
Assistant Examiner—Vickie Kim
(74) Attorney, Agent, or Firm—Carol A. Loeschorn

(57) ABSTRACT

This invention provides a topical composition, in the form of an emulsion, that comprises a compound of the FK506 class; a physiologically acceptable alkanediol, ether diol or diether alcohol containing up to 8 carbon atoms as solvent for the compound of the FK506 class; an unsaturated fatty alcohol and water.

In another aspect, this invention provides a topical pharmaceutical composition that comprises a macrolide in suspension.

In a further aspect, this invention provides the use of an unsaturated fatty alcohol to stabilize a macrolide in a pharmaceutical composition.

13 Claims, No Drawings

PHARMACEUTICAL COMPOSITIONS

This is a continuation of Ser. No. 09/488,283, filed Jan. 20, 2000, pending, which is a continuation of Ser. No. 09/302,763, filed Apr. 30, 1999, now abandoned, which is a continuation of Ser. No. 08/836,091, filed Apr. 25, 1997, now abandoned.

The present invention relates to topical pharmaceutical compositions comprising a macrolide, and in particular to formulations which comprise a macrolide such as an ascomycin, a rapamycin or a compound of the FK506 class.

FK506 is a known macrolide antibiotic that is produced by *Streptomyces tsukubaensis* No 9993. It is also a potent immunosuppressant. The structure of FK506 is given in the appendix to the Merck Index, 11th Edition as item A5. Methods of preparing FK506 are described in EP 184162.

A large number of derivatives, antagonists, agonists and analogues of FK506, which retain the basic structure and at least one of the biological properties (for example immunological properties) of FK506, are now known. These compounds are described in a large number of publications, for example EP 184162, EP 315978, EP 323042, EP 423714, EP 427680, EP 465426, EP 474126, WO 91/13889, WO 91/19495, EP 484936, EP 532088, EP 532089, EP 569337, EP 626385, WO 93/5059 and the like. These compounds are termed collectively compounds of the FK506 class.

It is also known (for example from EP 315978 and EP 474126) that compounds of the FK506 class are extremely useful in the topical treatment of inflammatory and hyperproliferative skin diseases and of cutaneous manifestations of immunologically-mediated illnesses.

Ointments containing a compound of the FK506 class and solubilizing and adsorption promoting agents to dissolve the compound are disclosed in EP 474126. Various organic solvents are proposed as solubilizing and adsorption promoting agents. However the compositions disclosed in EP 474126 are oil based compositions and do not contain water.

Compositions that contain water have been reported in the literature and FK506 compounds have also been formulated as fine suspensions (EP 484936).

It has now been surprisingly found that compounds of the FK506 class can be formulated into stable emulsions. Emulsions, since they contain an aqueous phase, are much less occlusive than oil-based compositions and hence are better tolerated in many situations.

Accordingly, in one aspect, this invention provides a topical composition, in the form of an emulsion, that comprises a compound of the FK506 class; a physiologically acceptable alkanediol, ether diol or diether alcohol containing up to 8 carbon atoms as solvent for the compound of the FK506 class; an unsaturated fatty alcohol and water.

This topical composition is effective, well tolerated on the skin, and reasonably to extremely stable.

In this specification, "a compound of the FK506 class" is a compound which has the same basic structure as FK506 and which has at least one of the biological properties of FK506 (for example immunosuppressant properties). The compound may be in free base form or pharmaceutically acceptable, acid addition, salt form. Examples of compounds of the FK506 class are compounds of the formula I

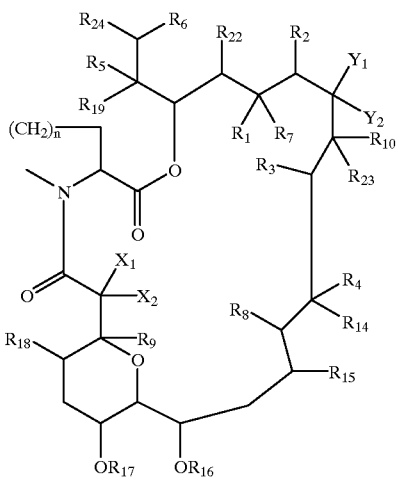

in which:
each adjacent pair of $R_1$ and $R_2$, $R_3$ and $R_4$, and $R_5$ and $R_6$ independently (a) is a pair of H atoms but $R_2$ may also be alkyl or (b) forms a second bond between the carbon atoms to which they are attached;

$R_7$ is H, OH, a protected OH group, a formyloxy group or an alkoxy group, or $R_7$ together with $R_1$ forms an oxo group;

$R_8$ and $R_9$ are independently H or OH;

$R_{10}$ is H, an alkyl group, an alkyl group substituted by one or more OH groups, an alkenyl group, an alkenyl group substituted by one or more OH groups, or an alkyl group substituted by an oxo group;

$X_1$ is H or OH;

$X_2$ is H; or $X_1$ and $X_2$ together are an oxo group or —$CH_2O$—;

$Y_1$ is H or OH;

$Y_2$ is H; or $Y_1$ and $Y_2$ together are an oxo group, N—$NR_{11}R_{12}$ or N—$OR_{13}$;

$R_{11}$ and $R_{12}$ independently are H, an alkyl group, an aryl group or a tosyl group;

$R_{13}$, $R_{14}$, $R_{15}$, $R_{16}$, $R_{17}$, $R_{18}$, $R_{19}$, $R_{22}$, and $R_{23}$ are independently H, or an alkyl group;

$R_{24}$ is an optionally substituted ring system which may contain one or more heteroatoms;

n is 1, 2 or 3;

or $Y_1$, $Y_2$, $R_{10}$ and $R_{23}$, together with the carbon atoms to which they are attached, are a saturated or unsaturated 5- or 6-membered nitrogen, sulphur and/or oxygen containing heterocyclic ring optionally substituted by one or more groups selected from alkyl, OH, alkoxy, benzyl, —$CH_2Se(C_6H_5)$ and alkyl substituted by one or more OH groups; in free base or in acid addition form.

Preferably $R_{24}$ is selected from (a) a 3,4-di-oxo-cyclohexyl group, (b) a 3-$R_{20}$-4-$R_{21}$-cyclohexyl group in which $R_{20}$ is OH, an alkoxy group, or a —$OCH_2OCH_2CH_2OCH_3$ group, and $R_{21}$ is OH, —OCN, an alkoxy group, a —$OCH_2OCH_2CH_2OCH_3$ group, a protected hydroxy group, chloro, bromo, iodo, methylthiomethoxy, isobutanoyloxy, aminooxalyloxy, an azido group, p-tolyloxythiocarbonyloxy or $R_{25}R_{26}$CHCOO— in which $R_{25}$ is optionally protected hydroxy or optionally protected amino and $R_{26}$ is H or methyl, or $R_{20}$ and $R_{21}$ together form an oxygen atom in an epoxide ring, or (c) a 5- or 6-membered cycloalkyl group which may be optionally substituted. For example $R_{24}$ may be a cyclopentyl group substituted by methoxymethyl, optionally protected hydroxymethyl, acyloxymethyl (in which the acyl moiety optionally contains either a dimethylamino group which may be quaternized, or a carboxy group which may be esterified), or one or more amino and/or hydroxy groups which may be protected, or aminooxalyloxymethyl. A preferred example is a 2-formyl-cyclopentyl group.

Suitable alkyl groups, alkenyl groups, aryl groups, protecting groups and acyl groups are defined in EP 484936.

The macrolide used in the compositions of the present invention preferably has immunosuppressant properties. The macrolide may be rapamycin or an O-substituted derivative in which the hydroxy in position 40 of formula A illustrated at page 1 of WO 95/16691, incorporated herein by reference, is replaced by —$OR_1$ in which $R_1$ is hydroxyalkyl hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)-rapamycin. These O-substituted derivatives may be produced by reacting Rapamycin (or dihydro or deoxorapamycin) with an organic radical attached to a leaving group (for example RX where R is the organic radical which is desired as the O-substituent, such as an alkyl, allyl, or benzyl moiety, and X is a leaving group such as $CCl_3C(NH)O$ or $CF_3SO_3$) under suitable reaction conditions. The conditions may be acidic or neutral conditions, for example in the presence of an acid like trifluoromethanesulfonic acid, camphorsulfonic acid, p-toluenesulfonic acid or their respective pyridinium or substituted pyridinium salts when X is $CCl_3C(NH)O$ or in the presence of a base like pyridine, a substituted pyridine, diisopropylethylamine or pentamethylpiperidine when X is $CF_3SO_3$.

A preferred compound is 40-0-(2-hydroxy)ethyl rapamycin (hereinafter compound A) as disclosed in WO 94/09010.

A preferred compound of the FK 506 class is disclosed in EP 427 680, e.g. Example 66a (also called 33-epi-chloro-33-desoxyascomycin) hereinafter compound B. Other preferred compounds of the FK 506 class are disclosed in EP 465 426, EP 569 337, and in EP 626 385, for example the compound of Example 6d in EP 569 337 hereinafter compound C, or the compound of Example 8 of EP 626385 hereinafter compound D.

Examples of alkanediol solvents which are capable of dissolving compounds of the FK506 class are propylene glycol (1,2-propanediol), butylene glycol, 2-ethyl-1,3-hexanediol, hexylene glycol (2-methyl-2,4-pentanediol) and the like. Examples of ether diol solvents are dipropyleneglycol, diethyleneglycol and the like. Examples of diether alcohol solvents are diethyleneglycol mono ethyl ether and the like. Preferably the solvent is hexylene glycol. The solvent is preferably present in an amount of about 5 to about 50% w/w, more preferably 5 to 20% w/w and even more preferably 5 to 10% w/w of the emulsion.

The oil phase of the emulsion may comprise about 20 to about 80% w/w, more preferably 25 to 75% and even more preferably 35 to 65% by weight of the composition. The emulsion may be an oil in water emulsion or a water in oil emulsion. The oil in water emulsion may be in the form of an emulsion gel (in which case the continuous aqueous phase may be thickened using a polymeric thickener), or in the form of a cream.

The unsaturated fatty alcohol forms part of the oil phase of the emulsion and is preferably a lanolin alcohol or a $C_{16}$ to $C_{18}$ fatty alcohol; more preferably oleyl alcohol, or elaidic alcohol, although oleyl alcohol is particularly preferred. The composition preferably contains sufficient amounts of the unsaturated fatty alcohol to promote absorption of the compound of the FK506 class in the skin, more preferably about 2 to about 10% w/w and even more preferably 5 to 10% w/w.

The oil phase also may contain other liquid oils, thickening agents and fatty bases usually used in topical compositions.

Suitable liquid oils include medium chain triglycerides obtained from fractionated vegetable oils, such as capryl/caprinic acid triglycerides. One example of such a triglyceride is commercially available under the trade name Miglyol 812 (which has a molecular weight of about 520, a $n_D^{20}$ of about 1.448 to 1.450 and a viscosity of 0.28 to 0.32 Pa.s). The liquid oil may comprise about 5 to about 60% w/w of the emulsion and preferably 5 to 15% w/w.

Suitable thickening agents include conventional stiffeners such as cetyl alcohol, cetostearyl alcohol, stearyl alcohol, hydrogenated castor oil (Cutina HR), Yellow wax, White wax, cetyl ester wax, emulsifying wax, microcrystalline wax, and the like. Preferably the thickening agent forms about 2 to about 30% w/w of the emulsion and more preferably 2 to 10% w/w.

Suitable fatty bases include bases such as natural wax, Vaseline (petroleum jelly, also available commercially as Petrolatum), thick paraffin, wool wax alcohols (such as those sold under the trade marks Eucerinum or Eucerin), wool wax derivatives, triglyceride waxes (such as that available under the trade name Softisan 378) and the like.

The composition may also include suitable emulsifiers as is usual in emulsion compositions. Such emulsifiers are described in standard texts such as Fiedler, H. P.; 1989; *Lexikon der Hilfsstoffe für Pharmazie, Kosmetic und angrenzende Gebiete*, Editio Cantor, D-7960 Aulendorf, Germany and *Handbook of Pharmaceutical Excipients*, A Joint Publication of the American Pharmaceutical Association, Washington DC, USA and the Pharmaceutical Society of Great Britain, London, UK; 1986. Examples of suitable emulsifiers include:

(a) propylene glycol mono- and di-fatty acid esters such as propylene glycol dicaprylate (which is commercially available under the trade mark Miglyol 840), propylene glycol dilaurate, propylene glycol hydroxystearate, propylene glycol isostearate, propylene glycol laurate, propylene glycol ricinoleate, and propylene glycol stearate;

(b) polyoxyethylene sorbitan fatty acid esters, such as mono- and tri-lauryl, palmityl, stearyl and oleyl esters. Examples of commercially available esters are those available under the trade name Tween (see Fiedler, pages 1300 to 1304) and particularly Tween 60 (polyoxyethylene(20) sorbitan mono stearate) and Tween 80 (polyoxyethylene(20) sorbitan mono oleate);

(c) polyoxyethylene fatty acid esters, for example polyoxyethylene stearic acid esters of the type known and commercially available under the trade name Myrj (See Fiedler, pages 834 and 835) and in particular Myrj 52 (which has a $D^{25}$ of about 1.1, a melting point of about 40 to 44° C., and a HLB value of about 16.9);

(d) Polyoxyethylene-polyoxypropylene co-polymers and block co-polymers such as those known and commercially available under the trade names Pluronic, Emkalyx and Poloxamer (see Fiedler, page 959) and in particular Pluronic F68 (which has a melting point of about 52° C. and a molecular weight of about 6800 to 8975) and Poloxamer 188;

(e) dioctylsulfosuccinate or di-[2-ethylhexyl]-succinate;
(f) phospholipids and in particular lecithins (see Fiedler, pages 943 and 944);
(g) salts of fatty alcohol sulphates such as sodium lauryl sulfate and sodium cetyl stearyl sulphate;
(h) sorbitan fatty acid esters such as sorbitan mono stearate and sorbitan mono oleate which are commercially available under the trade marks Arlacel 60 (which has an HLB of about 4.7 and a melting point of about 53° C.) and Span 80 (which has a $D^{25}$ of about 1, an HLB of about 4.3 and a viscosity of about 950 to 1100 cP); (i) glycerine mono stearate with is available under the trade name ]mwitor (see Fiedler, page 645) and particularly mwitor 960;
(j) esters of polyethylene-glycol glycerol ethers, that have at least one free hydroxyl group, and aliphatic $C_6$–$C_{22}$ carboxylic acids. Examples include PEG-20 glycerine mono stearate;
(k) reaction products of a natural or hydrogenated castor oil and ethylene oxide and of which examples are available under the trade name Cremophor such as Cremophor RH 40 (having a saponification no. of about 50 to 60, an acid number of <1, an $n_D^{60}$ of about 1.453 to 1.457 and an HLB value of about 14 to 16), Cremophor RH 60 (having a saponification no. of about 40 to 50, an acid number of <1, an $n_D^{25}$ of about 1.453 to 1.457 and an HLB value of about 15 to 17) and Cremophor EL (having a saponification no. of about 65 to 70, an acid number of about 2, an $n_{D25}$ of about 1.471 and a molecular weight of about 1630). Also suitable are various tensides available under the trade names Nikkol, Emulgin, Mapeg and Incrocas (see Fiedler);
(l) stearic acid;
(m) oil and wax based emulsifiers such as cetyl alcohol and emulsifying wax;
(n) polyoxyethylene glycerides such as those available under the trade name Labrafil M2130 CS (See Fiedler, page 707);
(o) polyoxyethylene alkyl ethers such as polyoxyethylene stearyl ether, polyoxyethylene oleyl ether and polyoxyethylene cetyl ether which are available under the Brij and Cetomacrogol series trade names (see Fiedler, pages 222 to 224 and 284);
(p) glycerine sorbitan fatty acid esters such as that available under the trade name Arlacel 481 (which has a molecular weight of about 630 and an HLB value of about 4.5) and
(q) mixtures thereof.

Preferably the emulsifier is selected from polyethyleneglycol (20) glycerine monostearate, sorbitan mono stearate (Arlacel 60), sorbitan mono oleate (Span 60), Tween 60, Tween 80, glycerine mono stearate (Imwitor 960), stearic acid, cetyl alcohol, wool wax derivatives and alcohols and Labrafil M2130 CS and mixtures thereof. If the emulsion is a water in oil emulsion, the emulsifier selected preferably has a HLB value of 10 to 15. If the emulsion is an oil in water emulsion, the emulsifier selected preferably has a HLB value of 4 to 8. Preferably the emulsifiers are present in an amount of about 1 to about 30% w/w and preferably 10 to 25% w/w.

Gelling agents may also be added to provide a gelled emulsion. Suitable gelling agents are carbomers (polyacrylic acid derivatives); such as those available under the trade name Carbopol (see Fiedler, pages 254 to 256). Carbopol 974 and Carbopol 1342 are preferred. The gelling agents are preferably present in an amount of 0.2 to 2% w/w; more preferably less than about 1% w/w.

The emulsion may also include preserving agents and anti-oxidants such as benzyl alcohol, butyl-hydroxytoluene, ascorbyl palmitate, sodium pyrosulphite, butyl hydroxy anisole, propyl p-hydroxybenzoate (available commercially, for example, under the trade name Paraben), methyl p-hydroxybenzoate (available commercially, e.g. as Paraben), sorbic acid and tocopherol. The preserving agents and anti-oxidants serve to prevent bacterial growth, and are preferably present in an amount of about 0.01 to about 2.5% w/w. pH modifying agents may be included to bring the pH of the emulsion to between 4 and 6 or by adding a pharmaceutically acceptable buffer system. A pH of between 4 and 6 is desirable to avoid skin irritation.

The aqueous phase of the emulsion may comprise about 20 to about 80% w/w, more preferably 25 to 75% and even more preferably 35 to 65% of the emulsion. The aqueous phase is preferably in the form of sterilized water.

The compound of the FK506 class is preferably present in the emulsion in an amount of about 0.01 to about 10% w/w and more preferably in an amount of 0.1 to 1% w/w.

Preferably the compound of the FK506 class and the unsaturated fatty alcohol are present in a weight ratio of 1:1000 to 5:1; preferably 1:100 to 1:5.

It has now been surprisingly found that macrolides can be formulated into stable pharmaceutical compositions, when the compounds are in suspensions.

Accordingly, in another aspect, this invention provides a topical pharmaceutical composition that comprises a macrolide in suspension.

The term macrolide has the meaning as described above.

The pharmaceutical composition may be in solid form, but preferably it is in semi solid form suitable for topical administration.

This suspension compositions of this invention are effective, well tolerated on skin, and reasonably to extremely stable.

The suspension contains particles of macrolide of from about 5, e.g from 10, to about 90 microns in diameter. The particles of the macrolide may be produced in conventional manner, e.g. by grinding or milling.

The suspension may be prepared as a cream, a water-free ointment, a water-in-oil emulsion, an oil-in-water emulsion, an emulsion gel or a gel.

In another aspect, this invention provides a topical composition in the form of an oil-in-water emulsion gel comprising a) a macrolide in an amount of up to 5 weight %,
b) a thickener in an amount of up to 20 weight %,
c) a hydrophilic component in an amount of up to 40 weight %,
d) one or more organic acids in a total amount of up to 5 weight %
e) one or more stabilisers in a total amount of up to 5 weight %,
f) water in an amount of up to 90% by weight.

Suitable thickeners are as defined above and may include paraffin, waxes, and petrolatum.

Appropriate hydrophilic components include propylene glycol, alcohols such as cetyl alcohol, stearyl alcohol and oleyl alcohol.

Examples of suitable organic acids contemplated for use in this invention include sorbic acid. The acid functions as a preservative and serves to substantially prevent bacterial growth.

In another aspect the invention provides a topical composition in the form of an emulsion or suspension as defined above for use in the treatment of inflammatory and hyperproliferative skin diseases and of cutaneous manifestations of immunologically-mediated diseases.

In another aspect the invention provides a method of treating inflammatory or hyperproliferative skin diseases or of cutaneous manifestations of immunologically-mediated diseases comprising administering a topical composition as defined above to the skin of a patient in need thereof.

In yet another aspect, the invention provides the use of a compound of the FK506 class; a physiologically acceptable alkanediol, ether diol or diether alcohol containing up to 8 carbon atoms as solvent for the compound of the FK506 class; an unsaturated fatty alcohol and water in the preparation of a medicament in the form of an emulsion for the treatment of inflammatory and hyperproliferative skin diseases and of cutaneous manifestations of immunologically-mediated diseases.

The emulsion compositions may be obtained by dissolving the compound of the FK506 class in the solvent and the unsaturated fatty alcohol to provide the oil phase. If desired liquid oils, fatty bases and thickening agents may be mixed into the oil phase. The oil phase is then emulsified with the aqueous phase and, if necessary, suitable emulsifiers. Other excipients may be added at the appropriate time to the appropriate phase as is conventional.

The present applicants have found that macrolides may be unstable in topical compositions. It is believed that this instability is caused by degradation or rearrangement pathways which are not completely understood. After extensive experimental work, the applicants have found that an unsaturated fatty alcohol may be used to stabilise macrolide compositions.

In a further aspect, this invention provides the use of an unsaturated fatty alcohol in stabilising a macrolide in a pharmaceutical composition.

In another aspect, this invention provides a method of stabilising a macrolide in a pharmaceutical composition, which method comprises mixing an unsaturated fatty alcohol with the macrolide.

The unsaturated fatty alcohol may be a $C_8$–$C_{22}$ alcohol, or may comprise a mixture of alcohols. The unsaturated fatty alcohol may have one, two or three double bonds. Preferably the unsaturated fatty alcohol has one double bond, and a cis configuration. Oleyl alcohol is preferred. A stabilising effect may be observed at a weight ratio of unsaturated fatty alcohol to active agent of at least about 1:5, for example 1:2 to 1:1 or greater, e.g. about 5:1.

The present applicants have found that the unsaturated fatty alcohol, e.g. oleyl alcohol, is suitable for stabilising a macrolide in a topical pharmaceutical composition. Examples of topical compositions are as described herein.

The unsaturated fatty alcohol, e.g. oleyl alcohol, may be used to stabilise a macrolide having at least one moiety as follows:

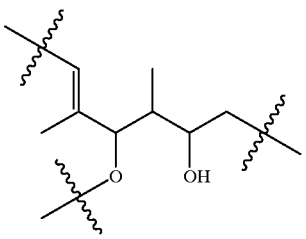

The present applicants have found that oleyl alcohol is useful in stabilising ascomycins and compounds of the FK 506 class, for example FK 506, ascomycin and 33-epi-chloro-33-desoxyascomycin.

The topical compositions defined above are useful in the treatment of inflammatory and hyperproliferative skin diseases and of cutaneous manifestations of immunologically-mediated diseases. Examples of such diseases are psoriasis, atopic dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematous and Alopecia areata.

The utility of the topical compositions can be observed in standard clinical tests such as the test set out in Example 12 infra using a concentration of 0.01 to 10% w/w (preferably 0.1 to 1% w/w) of the compound of the FK506 class. The utility can also be observed using standard animals models as described in EP 315978.

The exact amount of the compound of the FK506 class and of the composition to be administered depends on several factors, for example the desired duration of treatment and the rate of release of the compound of the FK506 class. Satisfactory results are obtained in larger mammals, for example humans, with the local application over the area to be treated of a 0.01 to 10% w/w, preferably 0.1 to 3%, concentration of the compound of the FK506 class once or several times a day (for example 2 to 5 times a day). In general the composition may be applied to areas of skin as small as 1 $cm^2$ to as large as 1 $m^2$. Suitable skin loadings of the compound of the FK506 class fall within the range of 0.1 $mg/cm^2$ to 1 $mg/cm^2$.

The compositions of this invention are well tolerated on skin. Good skin penetration and permeation rates may be achieved using the compositions of this invention.

The compositions described in Examples 13, 14 and 19 infra are preferred emulsion compositions for application to mammals, e.g. humans.

For the compounds (i) [3S-[3R*[E(1S*,3S*,4S*)],4S*,-5R*,8S*,9E,12R*,14R*,15S*,16R*,18S*,-19S*,26aR*]]-5,6,8,11,12,13,14,15,16,17,18,19,24,25,26,26a-hexadecahydro-5,19-dihydroxy-3-[2-(4-hydroxy-3-methoxy-cyclohexyl)- 1-methylethenyl)]-14,16-dimethoxy-4,10,12,18,-tetramethyl-8-(2-propenyl)-15,19-epoxy-3H-pyrido[2,1-c][1,4]oxaazacyclotricosine-1,7,20,21(4H,23H)-tetrone, (ii) [3S-[3R*[E(1S*,3S*,4S*)],4S*,-5R*,8S*,9E,12R*,14R*,15S*,16R*,18S*,-19S*,26aR*]]-5,6,8,11,12,13,14,15,16,17,18,19,24,25,26,26a-hexadecahydro-5,19-dihydroxy-3-[2-(4-hydroxy-3-methoxy-cyclohexyl)-1-methylethenyl)]-14,16-dimethoxy-4,10,12,18, -tetramethyl-8-ethyl-15,19-epoxy-3H-pyrido[2,1-c][1,4)oxaazacyclotricosine-1,7,20,21(4H,23H)-tetrone, and (iii) [3S-[3R*[E(1S*,3S*,4S*)],4S*,5R*,8S*,9E,12R*,-14R*,15S*,16R*,18S*,19S*,26aR*]]-5,6,8,11,12,13,14,15,16,-17,18,19,24,25,26,26a-hexadecahydro-5,19-dihydroxy-3-(3-hydroxymethylcyclopentyl)-1-methylethenyl)]-14,16-dimethoxy-4,10,12,18,-tetramethyl-8-ethyl-15,19-epoxy-3H-pyrido[2,1-c][1,4]oxaazacyclotricosine-1,7,20,21(4H,23H)-tetrone, topical application of concentrations of 0.01 to 1% w/w once a day is effective in the treatment of chronic plaque psoriasis in humans. In these applications the compositions are as effective as the ultra-potent Clobetasol composition (0.05%).

The following Examples describe compositions of this invention.

In the Examples, "Compound 1" is the compound [3S-[3R*[E(1S*,3S*,4S*)],4S*,5R*,8S*,9E,12R*,14R*,15S*,16R*,18S*,19S*,26aR*]]-5,6,8,11,12,13,14,15,16,17,18,19,24,25,26,26a-hexadecahydro-5,19-dihydroxy-3-[2-(4-hydroxy-3-methoxy-cyclohexyl)-1-methylethenyl)]-14,16-dimethoxy-4,10,12,18,-tetramethyl-8-(2-propenyl)-15,19-epoxy-3H-pyrido[2,1-c][1,4]oxaazacyclotricosine-1,7,20,21(4H,23H)-tetrone. This compound is better known as FK506.

"Compound 2" is the compound [3S-[3R*[E(1S*,3S*, 4S*)],4S*,5R*,8S*,9E,12R*,-14R*,15S*,16R*,18S*,19S*, 26aR*]]-5,6,8,11,12,13,14,15,16,17,18,19,24,25,26,26a-hexadecahydro-5,19-dihydroxy-3-(3-hydroxymethylcyclopentyl)-1-methylethenyl)]-14,16-dimethoxy-4,10,12,18,-tetramethyl-8-ethyl-15,19-epoxy-3H-pyrido[2,1-c][1,4]oxaazacyclotricosine-1,7,20,21(4H, 23H)-tetrone. This compound and a method of producing it are described in EP 465426.

"Compound 3" is [3S-[3R*[E(1S*,3S*,4S*)],4S*,5R*, 8S*,9E,12R*,14R*,15S*,16R*,18S*,-19S*,26aR*]]-5,6,8, 11,12,13,14,15,16,17,18,19,24,25,26,26a-hexadecahydro-5, 19-dihydroxy-3-[2-(4-hydroxy-3-methoxy-cyclohexyl)-1-methylethenyl)]-14,16-dimethoxy4,10,12,18, -tetramethyl-8-ethyl-15,19-epoxy-3H-pyrido[2,1-c][1,4] oxaazacyclotricosine-1,7,20,21(4H,23H)-tetrone. This compound is known as ascomycin.

Compound A, compound B, compound C and compound D have the respective meanings as described above.

The term stable, as used in the, following Examples, will be understood to mean that no separation of components is observed of the respective composition when stored at room temperature for a period of four months or longer.

Chemical analysis of the active agent is undertaken using reverse phase HPLC with UV detection; $\lambda=210$ nm. Quantification limit is 0.1% by weight.

Tolerability of the compositions is carried out, in vivo, on pig skin and on human skin. A visual assessment is made at 0.5, 1, 2 and 4 hours after application.

EXAMPLE 1

An oil in water emulsion is prepared containing the following ingredients (in parts by weight):

| | |
|---|---|
| Compound 2 | 0.10 |
| Oleyl alcohol | 10.00 |
| Miglyol 812 | 10.00 |
| Hexylene glycol | 10.00 |
| Cetyl alcohol | 5.00 |
| Stearyl alcohol | 5.00 |
| Benzyl alcohol | 1.00 |
| Sorbitan mono stearate | 2.00 |
| Tween 80 | 4.00 |
| Glycerine mono stearate | 3.00 |
| Water | 49.90 |

The composition is prepared by mixing together the compound 2, the oleyl alcohol, the Miglyol 812, the hexylene glycol, the cetyl alcohol and the stearyl alcohol and heating to 65° C. until all components are dissolved. The Arlacel 60, Tween 80 (polyoxyethylene(20)sorbitanmonooleate) and glycerine mono stearate are then added to the oil phase and stirred until all components are dissolved. The water is then heated in a vessel containing a stirrer and homogenizer. The benzyl alcohol is then added. The oil phase is then slowly added while stirring and homogenizing until a homogenous emulsion with a droplet size of less than 20 μm is obtained. The emulsion is then cooled to room temperature. The emulsion is stable.

EXAMPLE 2

An oil in water emulsion is prepared in a manner analogous to that in Example 1, and containing the following ingredients (in parts by weight):

| | |
|---|---|
| Compound 1 | 0.10 |
| Oleyl alcohol | 10.00 |
| Miglyol 812 | 10.00 |
| Hexylene glycol | 10.00 |
| Cetyl alcohol | 5.00 |
| Stearyl alcohol | 5.00 |
| Benzyl alcohol | 1.00 |
| Sorbitan mono stearate | 2.00 |
| Tween 80 | 4.00 |
| Glycerine mono stearate | 3.00 |
| Water | 49.90 |

The emulsion is stable. No component separation is observed.

EXAMPLE 3

A water in oil emulsion is prepared in a manner analogous to that in Example 1 except that the water is added slowly to the oil phase. The composition contains the following ingredients (in parts by weight):

| | |
|---|---|
| Compound 2 | 0.10 |
| Oleyl alcohol | 5.00 |
| Hexylene glycol | 5.00 |
| Yellow wax | 3.00 |
| Benzyl alcohol | 1.00 |
| Arlacel 481 | 7.00 |
| White Petroleum | 15.00 |
| Thick Paraffin | 5.00 |
| Water | 58.4 |
| $MgSO_4.7H_2O$ | 0.5 |

The emulsion is stable.

EXAMPLE 4

An oil in water emulsion is prepared in a manner analogous to that in Example 1, and containing the following ingredients (in parts by weight):

| | |
|---|---|
| Compound 2 | 0.10 |
| Oleyl alcohol | 7.50 |
| PEG-glycerine monostearate | 7.00 |
| propylene glycol | 10.00 |
| Cetyl alcohol | 6.00 |
| Glycerine mono stearate | 4.00 |
| Paraffin (thick) | 10.00 |
| White Petroleum | 15.50 |
| Sorbic acid | 0.01 |
| Water | 39.89 |

EXAMPLE 5, 6 and 7

Oil in water emulsions are prepared in a manner analogous to that in Example 1, and containing the following ingredients (in parts by weight):

| Example | 5 | 6 | 7 |
|---|---|---|---|
| Compound 2 | 1.00 | | |
| Compound 1 | | 0.10 | 1.00 |
| Oleyl alcohol | 7.50 | 7.50 | 7.50 |
| PEG-glycerine monostearate | 7.00 | 7.00 | 7.00 |

-continued

| Example | 5 | 6 | 7 |
|---|---|---|---|
| propylene glycol | 10.00 | 10.00 | 10.00 |
| Cetyl alcohol | 6.00 | 6.00 | 6.00 |
| Glycerine mono stearate | 4.00 | 4.00 | 4.00 |
| Paraffin (thick) | 10.00 | 10.00 | 10.00 |
| White Petroleum | 15.50 | 15.50 | 15.50 |
| Sorbic acid | 0.01 | 0.01 | 0.01 |
| Water | 38.99 | 39.89 | 38.99 |

EXAMPLES 8 to 11

The following emulsions are prepared in an analogous manner to that in Example 1.

| Example | 8 | 9 | 10 | 11 |
|---|---|---|---|---|
| Compound 3 | 0.10 | 0.10 | 0.10 | 0.10 |
| Hexylene glycol | 5.00 | 10.00 | 10.00 | 5.00 |
| Cetyl palmitate | 2.00 | — | — | — |
| Oleyl alcohol | — | 10.00 | 10.00 | — |
| Lanolin alcohols | — | — | — | 1.50 |
| MC* triglycerides | — | 10.00 | 10.00 | 5.00 |
| Isopropyl myristate | 8.00 | — | — | — |
| Cetyl alcohol | 4.00 | 5.00 | 5.00 | 2.00 |
| Stearyl alcohol | 4.00 | 5.00 | — | 2.00 |
| Benzyl alcohol | 1.00 | 1.00 | 1.00 | 1.00 |
| Sorbitan monostearate | 1.90 | 2.00 | — | 3.00 |
| Sorbitan monooleate | — | 4.00 | — | — |
| Glycerin monostearate | — | 3.00 | 10.00 | — |
| Tween 80 | 6.10 | — | — | — |
| Petroleum, white | — | — | — | 23.50 |
| Water | 67.90 | 49.90 | 53.90 | 56.40 |
| Magnesium sulfate, heptahydrate | — | — | — | 0.50 |

*MC = medium chain, e.g. Miglyol 812.

The compositions of Examples 4 to 11 are stable.

EXAMPLE 12

A single centre, double-blind, placebo-controlled trial is conducted to determine the efficacy of the compositions of Examples 4 to 7 in chronic plaque psoriasis. 10 patients who are over 18 years of age, have chronic plaque psoriasis and who have not had systemic or topical therapy for chronic plaque psoriasis, within 1 month and 1 week respectively, are chosen. On day -1, scales are removed with a topical composition containing 10% salicylic acid in Vaseline. On day 0, the compositions of examples 4 to 7, a 0.05% Clobetasol composition available under the trade mark Dermovate and a placebo are applied to the desquamated plaques under semi-occlusive conditions and left for 24 hours.

The patient is allowed to bath and the lesions are dried gently. The lesions are evaluated visually (erythema) and by palpation (infiltration) with scores ranging from of 0 (absent) to 3 (severe). The procedure is repeated daily until the 10/11 day.

The cumulative scores are presented in tables 1 and 2.

TABLE 1

| | Erythema Scores | | | | | | |
|---|---|---|---|---|---|---|---|
| day | 0 | 2 | 4 | 6 | 8 | 10 | 11 |
| Example 3 | 30 | 20.5 | 15 | 11.5 | 9 | 6 | 7.5 |
| Example 4 | 30 | 21.5 | 17.0 | 12 | 9.5 | 6 | 6.5 |
| Example 5 | 30 | 22 | 17 | 11 | 8 | 5.5 | 5 |
| Example 6 | 30 | 20 | 15.5 | 10 | 8.5 | 4.5 | 4.5 |
| Placebo | 30 | 28 | 25.5 | 25 | 23 | 23 | 22.5 |
| Dermovate | 30 | 20 | 13.5 | 10.5 | 8.5 | 8.0 | 8.0 |

TABLE 2

| | Infiltration Scores | | | | | | |
|---|---|---|---|---|---|---|---|
| day | 0 | 2 | 4 | 6 | 8 | 10 | 11 |
| Example 3 | 30 | 21 | 15.5 | 12 | 5.5 | 2 | 3 |
| Example 4 | 30 | 24 | 16.5 | 12 | 6.5 | 3 | 2.5 |
| Example 5 | 30 | 21.5 | 17 | 12 | 5 | 2 | 2 |
| Example 6 | 30 | 21.5 | 14.5 | 10 | 5.5 | 2.5 | 1.5 |
| Placebo | 30 | 28.5 | 24.5 | 23 | 21 | 19 | 18.5 |
| Dermovate | 30 | 19 | 14 | 8 | 3.5 | 2 | 2.5 |

No adverse events are observed with the compositions of examples 4 to 7 but skin atrophy is observed in 2 patients receiving Dermovate. However the compositions of examples 4 to 7 are at least as effective as Dermovate.

The active agent used in the compositions described in Examples 1 to 11 may be replaced by Compound A, B, C or D.

EXAMPLES 13 to 16

Oil in water emulsions are prepared in analogous manner to Example 1 and having the following compositions.

| Example | 13 | 14 | 15 | 16 |
|---|---|---|---|---|
| Oleyl alcohol | 10 | 10 | 10 | 10 |
| Miglyol 812 | 15 | 15 | 15 | 15 |
| Cetyl alcohol | 4 | 4 | | |
| Stearyl alcohol | 4 | 4 | | |
| Glycerol monostearate | 2 | 2 | | |
| Sorbitan monostearate | 3 | | | |
| Polysorbate 20 | | | 5 | |
| Polysorbate 60 | 5 | | | |
| Sodium cetylstearyl sulphate | | 1 | | |
| Methyl Paraben | 0.07 | 0.07 | 0.07 | 0.07 |
| Propyl Paraben | 0.03 | 0.03 | 0.03 | 0.03 |
| Carbopol 974p | | | 1 | 0.3 |
| Carbopol 1382 | | | | 0.7 |
| Compound B | 0.3 | 0.3 | 0.3 | 0.3 |
| Citrate buffer pH 5.5 | 0.05 | 0.05 | | |
| Propylene glycol | 5 | 5 | 10 | 10 |
| aqueous NaOH 5% wt/vol | | | 2.5 | 2.5 |
| Water | to 100 | to 100 | to 100 | to 100 |

The compositions of Examples 13 to 16 are well-tolerated on pig skin and on human skin. Assay of main degradation product is 0.1% (quantification limit) for compositions 15 and 16 after 72 hours at 70° C.; the oleyl alcohol is replaced by Miglyol 812 and assay of main degradation product increases to 0.5%. No separation of components is observed when stored at room temperature for four months.

EXAMPLES 17 to 19

Oil in water emulsion compositions are prepared having 1 wt-% active agent.

| Example | 17 | 18 | 19 |
|---|---|---|---|
| Oleyl alcohol | 2.5 | 5 | 10 |
| Miglyol 812 | 22.5 | 20 | 15 |
| Cetyl alcohol | 4 | 4 | 4 |
| Stearyl alcohol | 4 | 4 | 4 |
| Glycerol monostearate | 2 | 2 | 2 |
| Sorbitan monostearate | 3 | 3 | 3 |
| Polysorbate 60 | 5 | 5 | 5 |
| Methyl Paraben | 0.07 | 0.07 | 0.07 |
| Propyl Paraben | 0.03 | 0.03 | 0.03 |
| Citric acid | 0.05 | 0.05 | 0.05 |
| NaOH 1 M abs. wt./100 g | 0.02 | 0.02 | 0.02 |
| Propylene glycol | 5 | 5 | 5 |
| Compound B | 1 | 1 | 1 |
| Demin. water | to 100 | to 100 | to 100 |

The emulsions of Examples 17, 18 and 19 are stable and no separation of components is observed. The compositions are found to be well-tolerated on human skin. The compositions are stored at 40° C. for eight weeks and chemical analysis undertaken using HPLC. Assay of main degradation product for compositions 17, 18 and 19 is 1.1%, 0.8% and 0.4% respectively.

In the compositions of Examples 13 to 19, the active agent compound B may be replaced by compound A, compound C, compound D, compound 1, compound 2 or compound 3.

EXAMPLE 20

An oil in water emulsion composition is prepared as a cream using compound C as active agent:

| Component | Amount weight-% |
|---|---|
| Compound C | 0.3 |
| hexylene glycol | 10 |
| oleyl alcohol | 10 |
| Miglyol 812 | 10 |
| methyl Paraben | 0.07 |
| propyl Paraben | 0.03 |
| cetylalcohol | 5 |
| glycerol monostearate | 10 |
| water | to 100 |

The cream is stable and no separation of components is observed.

EXAMPLES 21 to 30

Suspension compositions are prepared in Examples 21 to 30.

EXAMPLE 21

A topical suspension composition is prepared containing the following ingredients (in parts by weight):

| Compound 1, 2, 3, A, B, C or D | 0.10 |
|---|---|
| Petroleum jelly | 99.9 |

The composition is prepared by mixing together the compound and other excipients.

Example 22

A single centre, double-blind, placebo-controlled trial is conducted to determine the efficacy of the compositions of Example 21 in chronic plaque psoriasis. 10 patients who are over 18 years of age, have chronic plaque psoriasis and who have not had systemic or topical therapy for chronic plaque psoriasis, within 1 month and 1 week respectively, are chosen. On day 1, scales are removed with a topical composition containing 10% salicylic acid in Vaseline. On day 0, the compositions of Example 21, a 0.05% Clobetasol composition available under the trade mark Dermovate and a placebo are applied to the desquamated plaques under semi-occlusive conditions and left for 24 hours.

The patient is allowed to bath and the lesions are dried gently. The lesions are evaluated visually (erythema) and by palpation (infiltration) with scores ranging from of 0 (absent) to 3 (severe). The procedure is repeated daily until the 10/11 day; clearing of psoriasis is observed.

Example 23

A topical suspension composition is prepared containing the following ingredients (in parts by weight) as an oil-in-water emulsion gel:

| Compound B | 0.3 |
|---|---|
| Paraffin, thick | 15 |
| glycerol monostearate | 0.3 |
| propylene glycol | 10 |
| Carbopol 974p | 0.5 |
| Carbopol 1342 | 0.5 |
| NaOH 5% | 2.5 |
| sorbic acid | 0.1 |
| water | 70.8 |

The composition is prepared by mixing together the compound and other ingredients. The composition is subjected to stress conditions in a centrifuge for 24 hours at a temperature of up to 95° C. No degradation of the active agent is observed using HPLC.

Suspension compositions are prepared in Examples 24 to 30.

| | Amount (g/100 g) |
|---|---|
| Example 24 | |
| Compound B | 0.1 |
| Paraffin, thick | 48 |
| Glycerol monostearate | 8 |
| Petrolatum, white | 43.9 |
| Example 25 | |
| Compound B | 0.1 |
| Paraffin, thin | 20 |
| Petrolatum, white | 71.9 |
| Wax, microcrystalline | 8 |
| Example 26 | |
| Paraffin, thick | 30 |
| Cetyl alcohol | 5 |
| Stearyl alcohol | 5 |
| Sorbitan monostearate | 2 |
| Polysorbate 80 (polyhydroxyethylen-sorbitanmonooleate) | 4 |
| Glycerol monostearate | 3 |
| Ascorbyl palmitate | 0.05 |
| Compound B | 0.1 |
| Sorbic acid | 0.1 |
| Propylene glycol | 5 |
| Water | 45.75 |

-continued

| | Amount (g/100 g) |
|---|---|
| Example 27 | |
| Propylene glycol | 10 |
| Paraffin, thick | 15 |
| Compound B | 0.1 |
| Carbopol 1342 (Polyacrylic acid, partly long chain alkylester) | 1 |
| Methyl Parabens | 0.07 |
| Propyl Parabens | 0.03 |
| NaOH aqueous solution 5% | 2.5 |
| Water | 71.30 |
| Example 28 | |
| Compound B | 0.1 |
| Carbopol 947 | 1 |
| NaOH aqueous solution 1 N | 2.5 |
| Water | 96.4 |
| Example 29 | |
| Compound B | 0.1 |
| Cetylstearyl alcohol | 0.5 |
| Wool wax alcohols | 6 |
| Petrolatum, white | 93.4 |
| Example 30 | |
| Compound B | 0.1 |
| Cetylstearyl alcohol | 0.25 |
| Wool wax alcohols | 3 |
| Petrolatum, white | 46.65 |
| Water | 50 |

Good to very good stability is observed for the suspension compositions of Examples 24 to 30. The suspensions are applied to healthy volunteers and are found to be well tolerated. Compound B may be replaced by compound 1, 2, 3, A, C or D in any of the compositions as described in Examples 23 to 30.

What is claimed is:

1. A topical composition, in the form of an emulsion, consisting essentially of an immunosupressant effective amount of 33-epi-chloro-33-desoxyascomycin, an alkanediol, ether diol, or diether alcohol containing up to 8 carbon atoms as solvent for the 33-epi-chloro-33-desoxyascomycin, a $C_8$–$C_{22}$ unsaturated fatty alcohol, water, a liquid oil, a thickening agent, an emulsifier and a preservative.

2. A topical composition according to claim 1 in which the solvent is hexylene glycol or propylene glycol.

3. A topical composition according to claim 1 wherein the unsaturated fatty alcohol is oleyl alcohol or elaidic alcohol.

4. A topical composition according to claim 1 wherein the unsaturated fatty alcohol contains one, two or three double bonds.

5. A topical composition according to claim 1 wherein the unsaturated fatty alcohol contains one double bond.

6. A topical composition according to claim 1 wherein the double bond has a cis configuration.

7. A topical composition, in the form of an emulsion, consisting essentially of 33-epi-chloro-33-desoxyascomycin; an alkanediol, ether diol, or diether alcohol containing up to 8 carbon atoms as solvent for the 33-epi-chloro-33-desoxyascomycin; a $C_8$–$C_{22}$ unsaturated fatty alcohol; water; a liquid oil; a thickening agent; an emulsifier; and a preservative, wherein the 33-epi-chloro-33-desoxyascomycin is present in the emulsion in an amount of about 0.01 to about 10% w/w.

8. A topical composition according to claim 7 wherein the 33-epi-chloro-33-desoxyascomycin is present in the emulsion in an amount of about 0.1 to about 1% w/w.

9. A topical composition according to claim 1 wherein the alkanediol solvent is selected from propylene glycol, butylene glycol, 2-ethyl-1,3-hexanediol and 2-methyl-2,4-pentanediol.

10. A topical composition according to claim 1 wherein the ether diol is selected from dipropylene glycol and diethylene glycol.

11. A topical composition according to claim 1 wherein the diether alcohol is diethylene glycol monoethyl ether.

12. A topical composition according to claim 1 wherein the unsaturated fatty alcohol is a lanolin alcohol or a $C_{16}$–$C_{18}$ fatty alcohol.

13. A topical composition according to claim 1 wherein the unsaturated fatty alcohol is oleyl alcohol.

* * * * *

UNITED STATES PATENT AND TRADEMARK OFFICE
CERTIFICATE OF CORRECTION

PATENT NO.    : 6,352,998 B2
DATED         : March 5, 2002
INVENTOR(S)   : Jackman et al.

It is certified that error appears in the above-identified patent and that said Letters Patent is hereby corrected as shown below:

Title page,
Item [63], should read:
-- Continuation of application No. 09/488,283, filed on Jan. 20, 2000, which is a continuation of application No. 09/302,763, filed on Apr. 30, 1999, now abandoned, which is a continuation of application No. 08/836,091, filed on Apr. 25, 1997, now abandoned, which is a 371 of application No. PCT/EP95/04208, filed on Oct. 26, 1995. --
After Item [63] please add:
-- Foreign Application Priority Data
  Oct. 26, 1994 (GB)    9421612.4
  Nov. 4, 1994  (GB)    9422306.2
  Feb. 22, 1995 (GB)    9503553.1 --

Column 5,
Line 13, "]mwitor" should read -- Imwitor --.
Line 14, "mwitor" should read -- Imwitor --.
Line 29, "$n_{D25}$" should read -- $n_D^{25}$ --.

Column 8,
Line 45, should read -- 8-ethyl-15, 19-epoxy-3H-pyrido[2,1-c][1,4] --.

Signed and Sealed this

Third Day of September, 2002

Attest:

Attesting Officer

JAMES E. ROGAN
*Director of the United States Patent and Trademark Office*